(12) United States Patent
Bodnar et al.

(10) Patent No.: US 11,779,214 B2
(45) Date of Patent: Oct. 10, 2023

(54) SYSTEMS AND METHODS FOR MEASURING AND CLASSIFYING OCULAR MISALIGNMENT

(71) Applicants: Zachary Bodnar, Las Vegas, NV (US); Heather Moss, Burlingame, CA (US); David Buickians, Burlingame, CA (US)

(72) Inventors: Zachary Bodnar, Las Vegas, NV (US); Heather Moss, Burlingame, CA (US); David Buickians, Burlingame, CA (US)

( * ) Notice: Subject to any disclaimer, the term of this patent is extended or adjusted under 35 U.S.C. 154(b) by 417 days.

(21) Appl. No.: 17/193,322

(22) Filed: Mar. 5, 2021

(65) Prior Publication Data
US 2021/0275018 A1 Sep. 9, 2021

Related U.S. Application Data

(60) Provisional application No. 62/986,415, filed on Mar. 6, 2020.

(51) Int. Cl.
*A61B 3/15* (2006.01)
*A61B 3/00* (2006.01)

(52) U.S. Cl.
CPC ............ *A61B 3/152* (2013.01); *A61B 3/0025* (2013.01); *A61B 3/0033* (2013.01); *A61B 3/0058* (2013.01); *A61B 2562/0219* (2013.01)

(58) Field of Classification Search
CPC ..... A61B 3/152; A61B 3/0025; A61B 3/0033; A61B 3/0058; A61B 2562/0219; A61B 3/085
USPC ....................................................... 351/206
See application file for complete search history.

(56) References Cited

U.S. PATENT DOCUMENTS

| | | | |
|---|---|---|---|
| 6,329,873 B2 * | 12/2001 | Morishita | G05F 1/465 327/541 |
| 6,392,873 B1 | 5/2002 | Honda | |
| 10,268,044 B1 * | 4/2019 | Spickermann | G02B 27/0176 |
| 2006/0087618 A1 * | 4/2006 | Smart | A61B 3/08 351/209 |
| 2015/0234189 A1 * | 8/2015 | Lyons | G02B 27/017 345/174 |

(Continued)

OTHER PUBLICATIONS

PCT/US2022/018715, International Search Report.
PCT/US2022/018715, Written Opinion.

*Primary Examiner* — Mohammed A Hasan
(74) *Attorney, Agent, or Firm* — CrossPond Law (57) ABSTRACT

A device for measuring and classifying ocular misalignment of a patient's eyes includes an enclosure, two lenses at the front of the enclosure, one corresponding to each eye of a patient, a divider within the enclosure, positioned laterally between the lenses, a screen within the enclosure, an integrated microprocessor connected to the screen, and at least one input control connected to the integrated microprocessor, at least one input control operable by the patient; where the integrated microprocessor generates and transmits two images to the screen, each image corresponding to each lens; where the integrated microprocessor receives input from the patient via at least one input control to manipulate at least one image on the screen; and where the integrated microprocessor calculates and outputs a quantification of ocular misalignment based on that input.

19 Claims, 8 Drawing Sheets

(56) References Cited

U.S. PATENT DOCUMENTS

| | | |
|---|---|---|
| 2016/0018853 A1* | 1/2016 | Buckley .................. G06F 3/017 |
| | | 345/174 |
| 2016/0224176 A1 | 8/2016 | Kim et al. |
| 2019/0046029 A1* | 2/2019 | Tomasi ................ G06V 40/193 |
| 2020/0117012 A1 | 4/2020 | Wen et al. |
| 2021/0275018 A1 | 9/2021 | Bodnar et al. |

* cited by examiner

SYSTEMS AND METHODS FOR MEASURING AND CLASSIFYING OCULAR MISALIGNMENT

This patent application is a utility application that claims the benefit of U.S. Provisional Patent Application Ser. No. 62/986,415, filed on Mar. 6, 2020, which is hereby incorporated by reference in its entirety.

FIELD OF THE INVENTION

This invention relates generally to the fields of ophthalmology, optometry, orthoptics, pediatrics and neurology, and more specifically to a new and useful system and method for detecting and measuring and the direction and amount of misalignment of the eyes, as well as categorizing the deviations detected into normal patterns or patterns associated with specific disorders of the oculomotor system.

BACKGROUND

The human visual system integrates visual signals from the retina as well as the vestibular apparatus in the inner ear to generate signals to the extraocular muscles that control movements to the eyes and eyelids in order to maintain binocular vision. Lesions in the brain, brainstem, the cranial nerves directing the extraocular muscles, or the extraocular muscles themselves can all result in misalignment of the eyes (strabismus). Example of such lesions include, but are not limited to stroke, intracranial vascular aneurysms, trauma, thyroid eye disease, demyelinating diseases, myasthenia gravis and congenital malformations. Misalignment of the eyes can also occur due to inadequate cortical stimulus for binocular fusion, such as uncorrected refractive error in one eye.

The cause of disorders of the oculomotor system can often be determined by the pattern of the resulting ocular deviation. One example is a left intranuclear ophthalmoplegia, in which the eye movements are completely normal except that the left eye cannot move to the right in right gaze. In some cases, identifying the correct pattern of ocular deviation can be critically important to rule out life-threatening emergencies such as carotid artery dissections or intracranial vascular aneurysms. The treatment of many disorders of ocular misalignment, often with surgery to strengthen, weaken or move the extraocular muscles, is also highly dependent on accurate measurement and characterization of the ocular misalignment. Critically, strabismus in children can lead to permanent loss of vision, including blindness, if untreated prior to critical developmental age (approximately 8 years).

Measurement of ocular misalignment must be done, at present, by highly-trained experts, such as pediatric ophthalmologists, neuro-ophthalmologists, or orthoptists. This measurement is referred to as the prism cover test (PCT), and is usually performed by placing prisms in front of the patient's eyes and analyzing the movement of the eyes as the patient is forced to alternate the eye used for fixation on a visual target. This is done in various positions of gaze, requiring the use of both near and distant fixation targets, and sometimes with the head tilted to one side or the other. The distant fixation target is approximately 6 m from the patient's eyes; as a result, the prism cover test requires a large space in which the test can be performed. The emerging pattern is interpreted by the expert examiner to make a diagnosis and guide treatment. The examiner also observes the eye movements, different directions of gaze, and grossly quantifies deficiencies to identify any restrictions in the extraocular muscles. Techniques involving specialized lenses also exist for measuring torsional misalignment (i.e., malrotation about the pupillary axis). Even when performed by experts, these techniques are inherently subjective and may be limited for pediatric patients and cognitively-impaired adults. Only one analog device exists that can perform objective measurement of all patterns of strabismus, the synoptophore, and it requires an expert operator.

Some forms of vertical strabismus can have deviations of different magnitudes depending on whether the head is vertical, tilted to the left or titled to the right. Measuring the deviation with different directions of head tilt is critical for identifying the affected neurologic pathway or muscles (the Parks-Bielschowsky three-step test). Additionally, torsional deviation may be minimized by tilting the head to one side or the other, and patients will naturally position their head accordingly to minimize diplopia. Therefore, the true torsional deviation can only be measured when taking into account head tilt. Additionally, some neurologic lesions may alter the patient's subjective sense of vertical and result in a head tilt in conjunction with a torsional deviation. However there are currently no devices that can simultaneously measure ocular deviation and head tilt.

Thus, there is a need for a device to objectively measure all patterns of strabismus while accounting for head position, without requiring an expert operator. This invention provides such a novel and useful method.

SUMMARY OF THE INVENTION

A device for measuring and classifying ocular misalignment may include an electronic display surrounded by a viewing enclosure with a central divider separating the images between the left and right eyes, referred to henceforth as "the viewer".

A device for measuring and classifying ocular misalignment of a patient's eyes may include an enclosure, two lenses at the front of the enclosure, one corresponding to each eye of a patient, a divider within the enclosure, positioned laterally between the lenses, a screen within the enclosure, an integrated microprocessor connected to the screen, and at least one input control connected to the integrated microprocessor, at least one input control operable by the patient; where the integrated microprocessor generates and transmits two images to the screen, each image corresponding to each lens; where the integrated microprocessor receives input from the patient via at least one input control to manipulate at least one image on the screen; and where the integrated microprocessor calculates and outputs a quantification of ocular misalignment based on that input.

A method for measuring and classifying ocular misalignment may include providing a viewer, which includes an enclosure, two lenses at the front of the enclosure, one corresponding to each eye of the patient, a divider within the enclosure, the divider positioned laterally between the lenses, and a screen within the enclosure; displaying on the screen two different images, one corresponding to each lens, where each eye of the patient sees a different image; receiving input from the patient, where the input aligns the images based on the patient's perception; and determining the misalignment between the images that remains after the receiving input.

DETAILED DESCRIPTION

A device for measuring and classifying ocular misalignment generally may include a viewing enclosure with at least one lens for each eye to focus the image from a display, and a divider to separate the images presented to each eye. The device also may include a microprocessor to control the display, process inputs from various sensors and from the user via buttons on the outside of the enclosure.

Figure 1A:
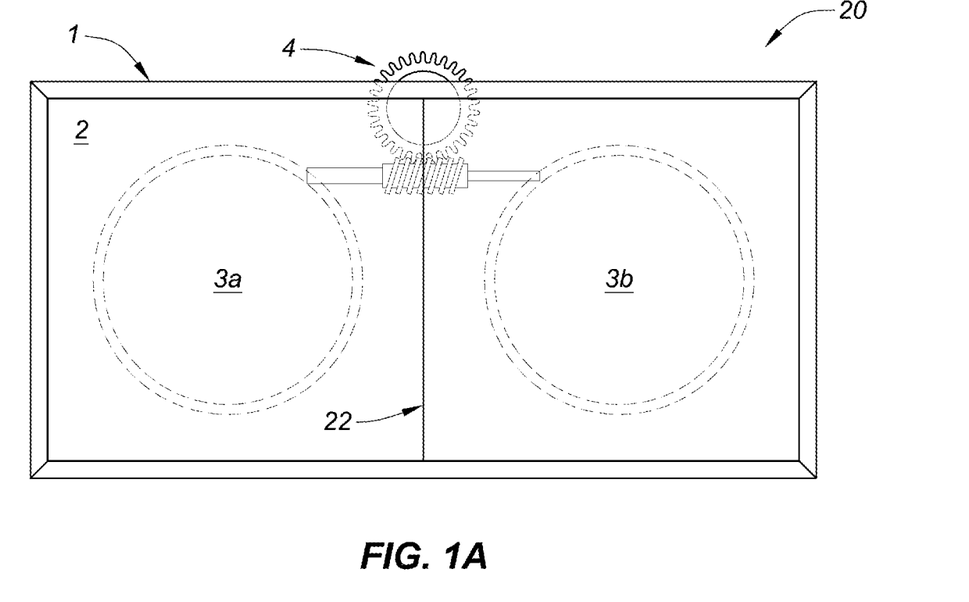
FIG. 1A is a front view of a viewer including a display.
Figure 1B:
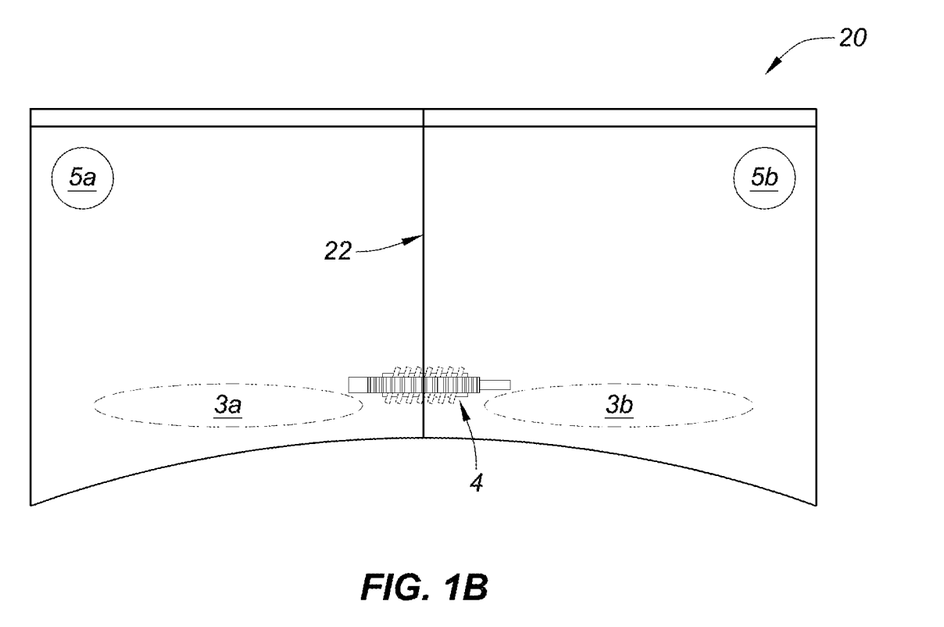
FIG. 1B is a top view of the viewer of FIG. 1A.
Figure 8:
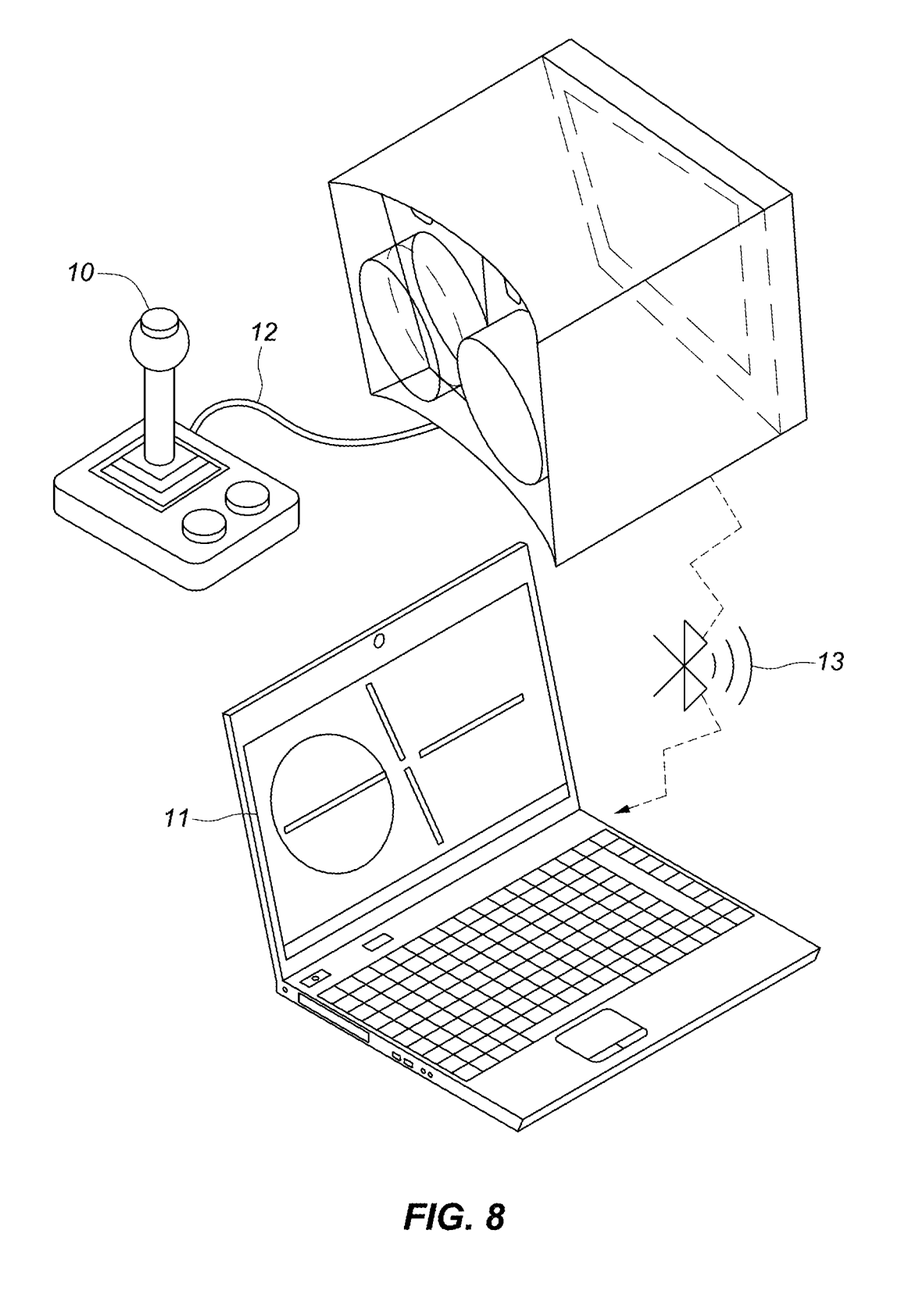
FIG. 8 is a perspective view of another embodiment of a viewer, in which input is provided to the viewer via a joystick, and data is output from the viewer to a computer.

Referring to FIGS. 1a-1b, one embodiment of a viewer 20 is shown. The viewer 20 includes a viewing enclosure 1, which may encase a screen 2 and lenses 3a,3b. As is standard terminology in the art, the lenses 3a, 3b may be referred to as oculars as well as lenses. A wheel and gear system 4 may be provided to allow the lateral position of the lenses 3a, 3b to be adjusted to match the interpupillary distance of the patient. According to other embodiments, the lateral position of the lenses 3a, 3b may be adjusted in any other suitable manner. The lenses 3a, 3b are separated from the screen 2 by any distance that is long enough to allow for a useful diagnostic process, and short enough so that the viewing enclosure 1 does not become cumbersome. As one example, the lenses 3a, 3b may be separated from the screen 2 by a distance that is substantially 3.8 cm. As another example, the lenses 3a, 3b may be separated from the screen 2 by a distance that is between substantially 3.7-3.9 cm. As another example, the lenses 3a, 3b may be separated from the screen 2 by a distance that is between substantially 3.5-4.0 cm. As another example, the lenses 3a, 3b may be separated from the screen 2 by a distance that is between substantially 3.0-4.5 cm. As another example, the lenses 3a, 3b may be separated from the screen by a distance of less than or equal to 10 cm, less than or equal to 15 cm, less than or equal to 20 cm, or less than or equal to 25 cm. One or more input controls are provided. As one example, the input controls are buttons 5a and 5b, located on an upper surface of the enclosure 1, and provide input to the device, as described in greater detail below. The buttons 5a, 5b alternately may be placed on a different location on the enclosure. According to other embodiments, the buttons 5a, 5b may be placed on a separate handheld device that is connected to the viewer 20 via a cord, via a wireless connection, or in any other suitable manner. Referring also to FIG. 8, as another example of an input control, an input control may be a joystick 10 used in conjunction with, or instead of, buttons 5a, 5b to provide input to the viewer 20. A divider 22 may be located laterally between the lenses 3a, 3b. The divider 22 may be substantially planar and substantially vertical. Advantageously, the divider 22 may be matte black to minimize or prevent light emitted from the screen from reflecting from either lateral surface of the screen 2. The divider 22 allows one screen to be used to display two separate images to the patient, one through each lens 3a, 3b. In this way, a separate and distinct image may be presented to each eye of the patient.

Figure 1C:
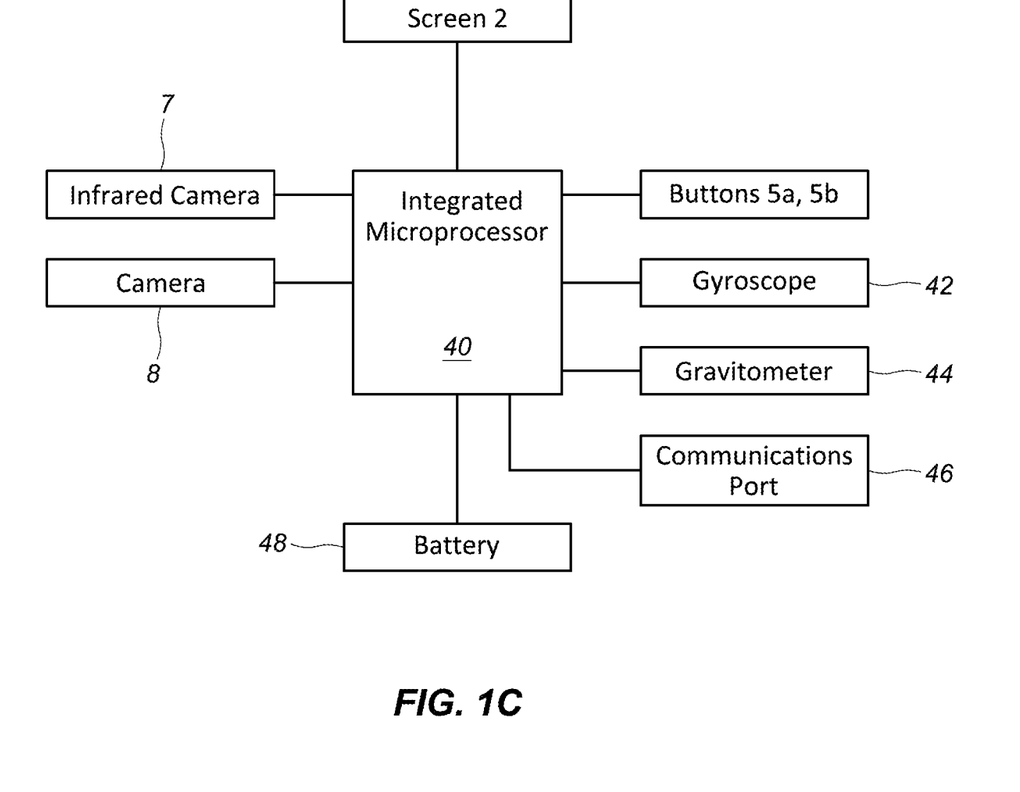
FIG. 1C is a schematic view of the viewer of FIGS. 1A-1B.

Referring also to FIG. 1C, one embodiment of the viewer 20 includes an integrated microprocessor 40 that is used to display images on the screen 2. An embodiment of the viewer may include at least one gyroscope 42 and/or at least one gravitometer 44. Where the enclosure 1 is configured to be worn by the patient, the gyroscope 42 and/or gravitometer 44 detect head motion of the patient, generate data corresponding to such head motion, and transmit that head motion data to the integrated microprocessor 40. The integrated microprocessor 40 also may receive other input from the patient, such as button presses from the buttons 5a, 5b. The integrated microprocessor 40 may output data to a secondary screen for use by the examiner, via at least one communications port 46. Each communications port 46 may be configured for wired or wireless connection to a secondary screen, such as a monitor, tablet, laptop computer or desktop computer. A battery 48 or other power source is connected to the integrated microprocessor 40 to provide power thereto.

Figure 6:
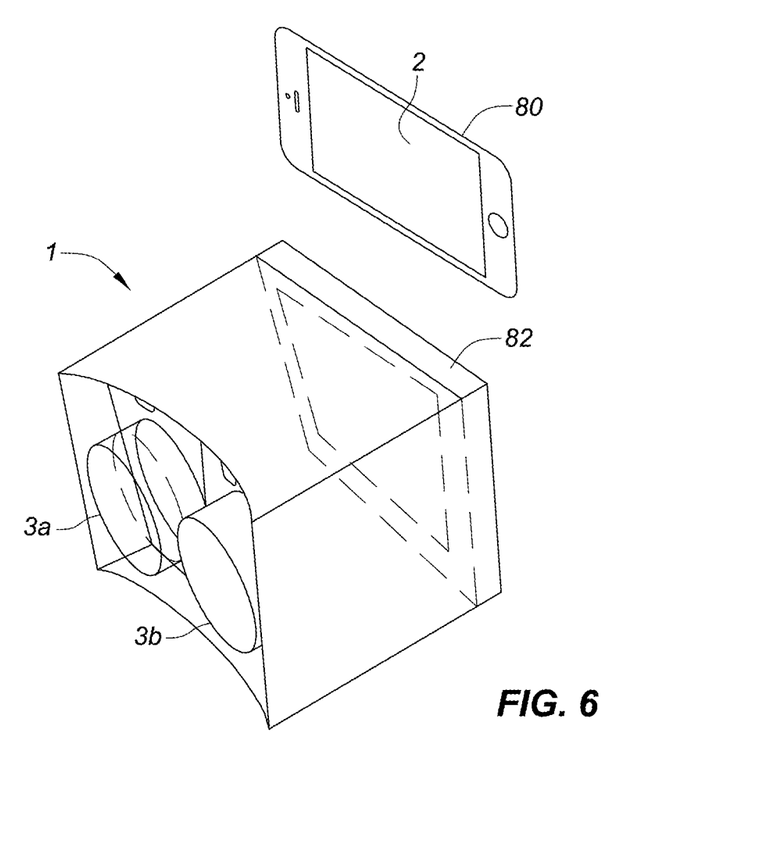
FIG. 6 is a perspective view of another embodiment of a viewer, in which a housing receives a smartphone within an enclosure.

Referring also to FIG. 6, the screen 2, gyroscope 42, gravitometer 44, integrated microprocessor 40 and/or communications port 46 may be provided by a smartphone or tablet 80. The smartphone or tablet 80 is inserted into the enclosure 1 into a receiver 82 in the enclosure 1, with the screen 2 facing the lenses 3a, 3b. The use of a smartphone or tablet 80 may increase the convenience of use of the viewer 20, and decrease the cost of the viewer 20 significantly, thereby enhancing access to screening for more patients.

In use, the enclosure 1 is placed in proximity to the patient's eyes, like a pair of goggles. The enclosure 1 may be connected to a strap or straps that allow the patient to wear the enclosure 1 during testing of his or her vision. By using the strap or straps, the enclosure 1 (and thus the viewer 20 as a whole) may be fixed substantially relative to the patient's head during the examination, facilitating the use of at least one gyroscope 42 and/or gravitometer 44 as part of the examination. According to other embodiments, the enclosure 1 may be held by the person administering the exam, may be mounted to a stand 9 such as a tripod (referring also to FIG. 7), or may be positioned or mounted in any other suitable manner. The stand 9 optionally may telescope and/or retract, and/or may be detachable from the viewer 20.

Figure 2:
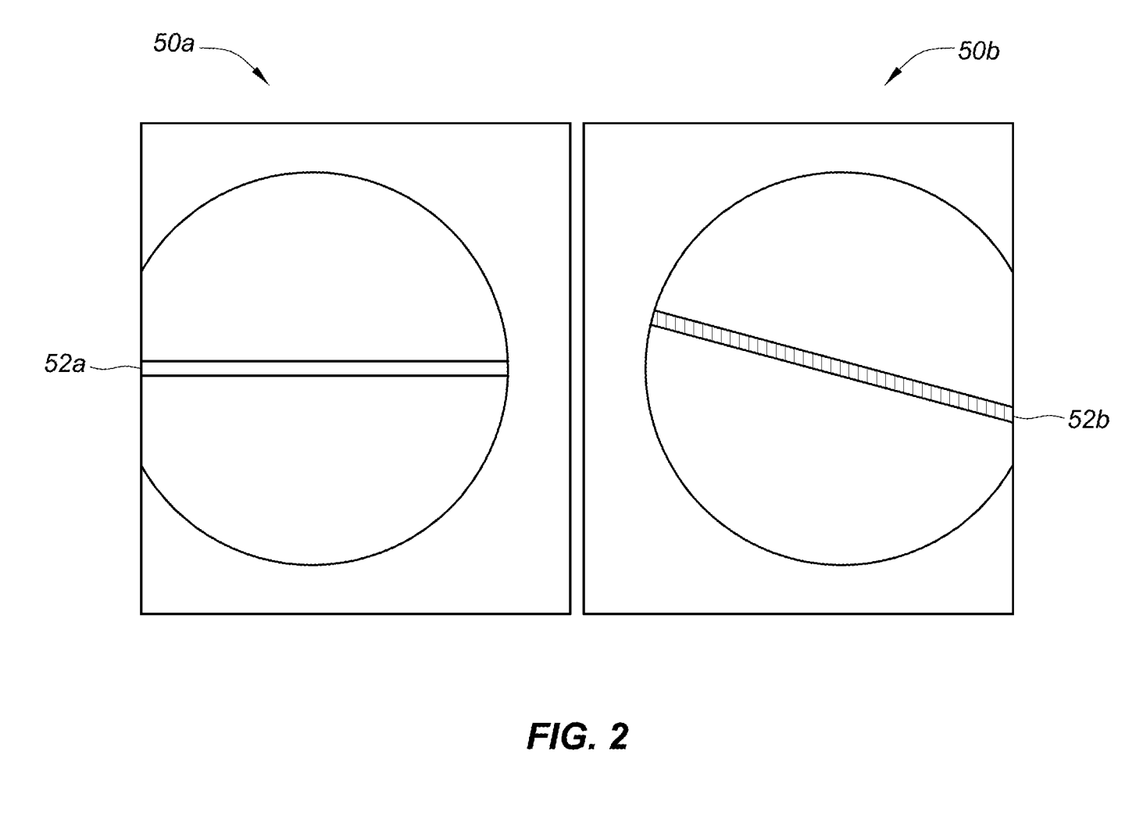
FIG. 2 is a first set of two images displayable on the display, showing two bars oriented at different angles, used to quantify torsional misalignment of a patient's eyes.

Referring also to FIG. 2, two images 50a, 50b are displayed on the screen 2, where those images 50a, 50b are used to quantify torsional misalignment of the patient's eyes. The images 50a, 50b are displayed on the screen 2, separated by the divider 22, such that the image 50a is viewed by the patient through lens 3a, and the image 50b is viewed by the patient through lens 3b. Each image 50a, 50b includes a bar 52a, 52b, where the bars 52a, 52b are shown rotated to different angles relative to one another. For example, FIG. 2 shows the bars 52a, 52b rotated 15 degrees relative to one another. Thus, as seen in FIG. 2, when displayed on the screen 2, the left eye of the patient sees bar 52a through the left lens 3a, and the right eye of the patient sees bar 52b through the right lens 3b. Torsional misalignment is quantified by making the bars appear parallel when viewed by the subject using the viewer 2. Using the buttons 5a, 5b, or other inputs, the subject's task is to rotate one of the images 50a, 50b until the two bars 52a, 52b appear to be parallel with each other. The residual disparity in rotation at the end of this task—that is, the angle between the two bars 52a, 52b when the patient perceives the two bars 52a, 52b to be parallel—is the angle of torsional misalignment between the patient's two eyes. That angle of torsional misalignment is calculated by the integrated microprocessor 40, and communicated by the integrated microprocessor to the examiner. If a head tilt is detected by the gyroscope 42 or gravitometer 44 during this test, it can be quantified and compared to the torsional ocular deviation, if present, to detect an ocular tilt reaction (aka skew deviation), indicative of a lesion somewhere along the pathway from the brainstem to the utricle of the inner ear.

Figure 3:
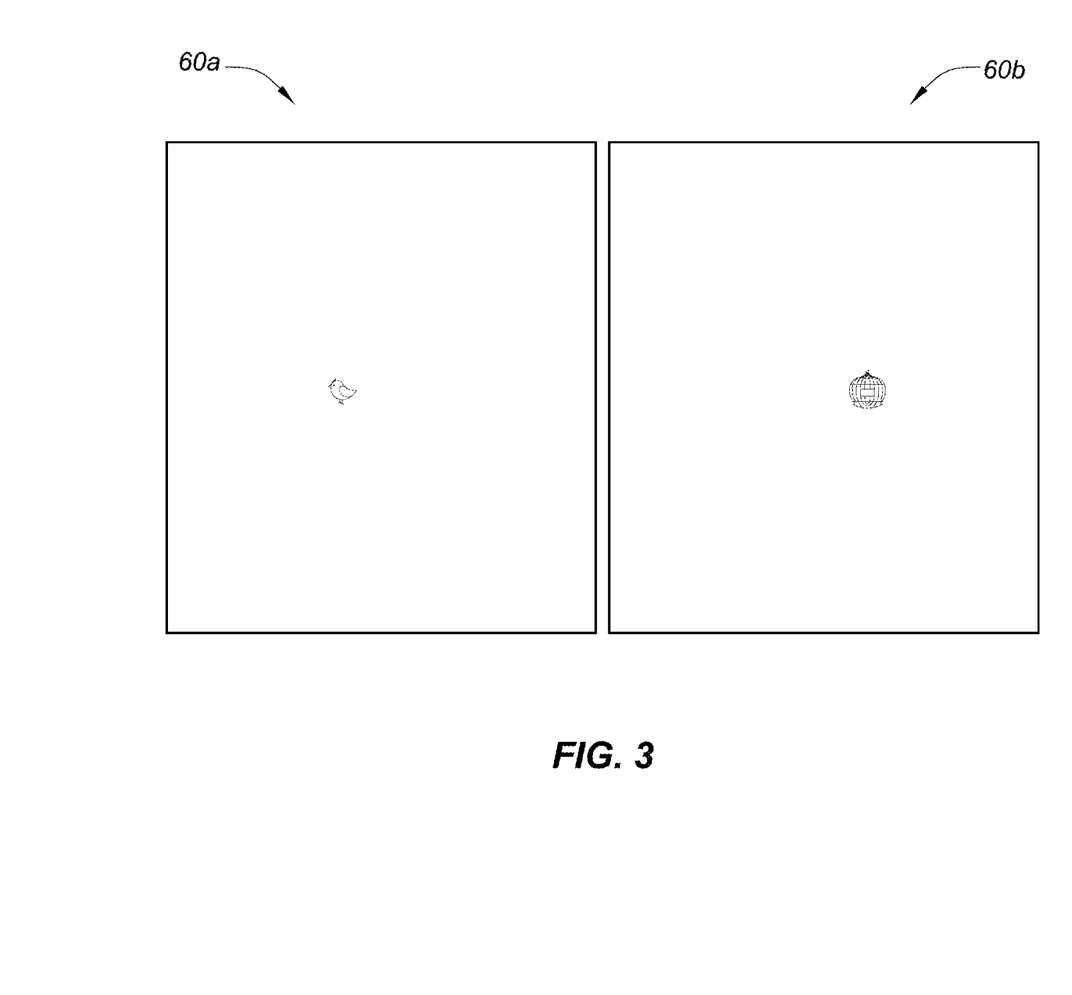
FIG. 3 is a second set of two images displayable on the display, showing a bird and a cage, used to quantify vertical and horizontal misalignment of a patient's eyes.

Referring also to FIG. 3, two images 60a, 60b are displayed on the screen 2, where those images 60a, 60b are used to quantify vertical and horizontal misalignment of the patient's eyes. The images 60a, 60b are displayed on the screen 2, separated by the divider 22, such that the image 60a is viewed by the patient through lens 3a, and the image 60b is viewed by the patient through lens 3b. The images 60a, 60b are different from one another and are located at different horizontal and/or vertical positions relative to one another. As seen in FIG. 3, the image 60a is a bird and the image 60b is a cage. According to other embodiments, the image 60a may be a cross and the image 60b may be a circle. Alternately, the images 60a, 60b may be any other suitable images. Thus, as seen in FIG. 3, when displayed on the screen 2, the left eye of the patient sees bird 60a through the left lens 3a, and the right eye of the patient sees cage 60b through the right lens 3b. Vertical and horizontal misalignment is quantified by moving the bird 60a into the cage 60b when viewed by the subject using the viewer 2. Using the buttons 5a, 5b, or other inputs, the subject's task is to move the bird 60a into the cage 60b; that is, to move the two images 60a, 60b into alignment with one another. The residual disparity in horizontal displacement between the images 60a, 60b at the end of this task—that is, the horizontal distance between the center of the bird 60a and the center of the cage 60b when the patient perceives the bird 60a to be centered in the cage 60b—is converted to an angle of horizontal deviation between the patient's two eyes. Similarly, the residual disparity in vertical displacement between the images 60a, 60b at the end of this task—that is, the vertical distance between the center of the bird 60a and the center of the cage 60b when the patient perceives the bird 60a to be centered in the cage 60b—is converted to an angle of vertical deviation between the patient's two eyes. The angles of horizontal and vertical deviation are calculated by the integrated microprocessor 40, and communicated by the integrated microprocessor to the examiner.

The angles of horizontal and vertical deviation may be calculated by the integrated microprocessor 40 in any suitable manner. As one example, the image of the bird 60a may be displaced $X_p$ pixels to the right from the location it would occupy if the patient exhibited no horizontal deviation. The resolution of the screen 2 in pixels/millimeter is known, so the distance of $X_p$ pixels can be converted to a distance of $X_m$ millimeters. The distance Z in millimeters from the eye to the screen 2 is also known, from the geometry of the viewing enclosure 1. The horizontal angle of deviation θ is then computed using the trigonometric equation $\tan θ = X_m/Z$. The sign of $X_m$ matters in the determination of the direction of rotation (in or out). The vertical deviation is calculated in an analogous manner.

When measuring vertical and horizontal displacement in the setting of a deviation, the subject will not be looking through the center of the lens 3a, 3b. The prismatic distortion that results will skew the measurements. For example, if the image of the cage 60b is displaced to the right it will appear to the patient to be even farther right than it actually is, and that distortion is non-linear. This distortion may be rectified by performing a transformation of the screen coordinates using the Brown-Conrady model of lens distortion, or other similar approach (Brown, Duane C. (May 1966). "Decentering distortion of lenses" Photogrammetric Engineering. 32 (3): 444-462, Conrady, A. E. (1919). "Decentered Lens-Systems". Monthly Notices of the Royal Astronomical Society. 79 (5): 384), which are hereby incorporated by reference in their entirety. Such a transformation is applied to the image coordinates before they are displayed to the patient on the screen 2, so that the images (such as the bird 60a and cage 60b) appear to the patient to move in a linear manner on the screen 2 as the patient adjusts them, and the calculation in the preceding paragraph is effective and accurate.

Figure 4:
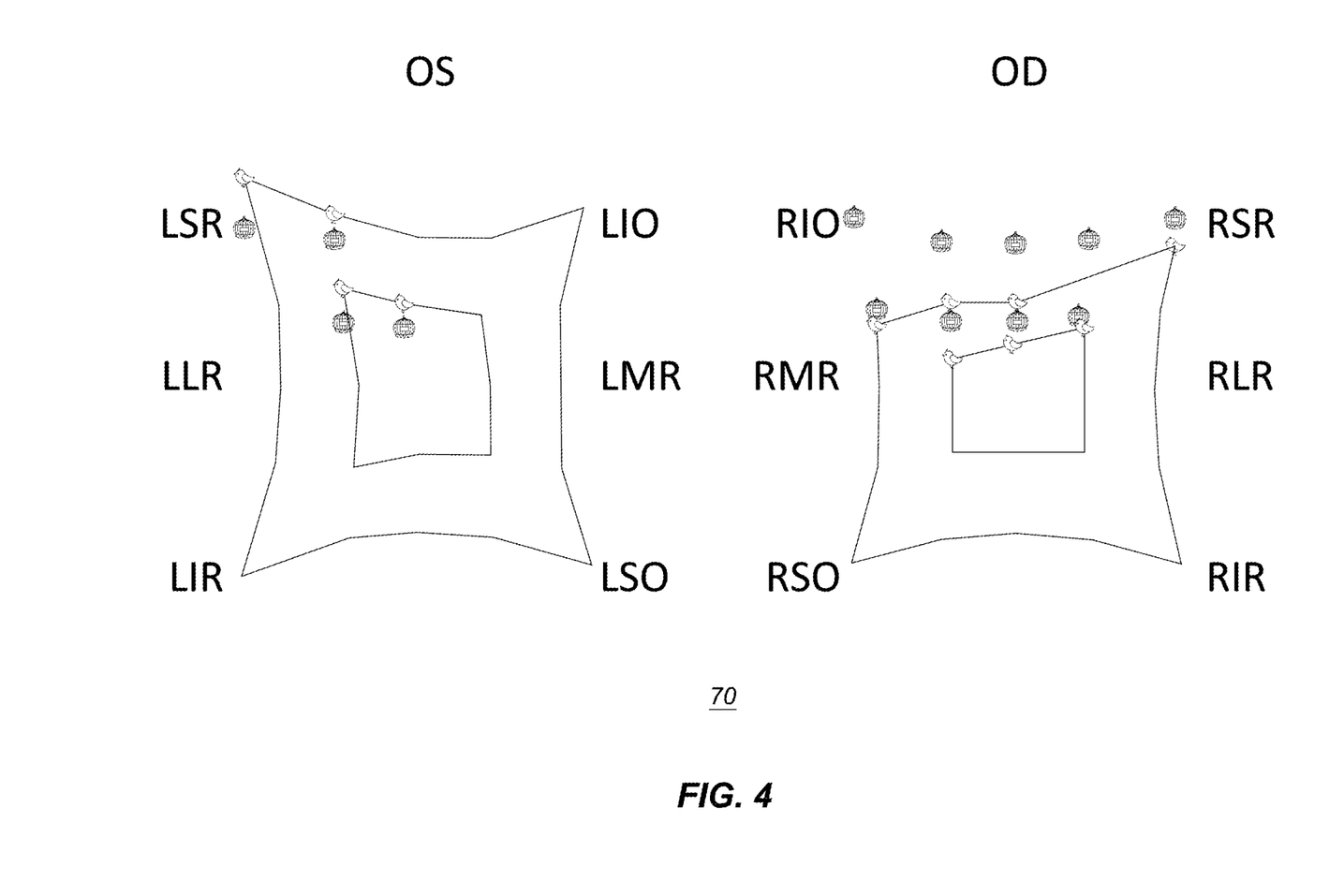
FIG. 4 is a Hess chart showing the results of an exemplary examination.

If there is a vertical deviation, additional measurements can also be performed with the head tilted to the left and to the right, with the gyroscope 42 and gravitometer 44 used to measure the angle of head tilt. The device can compare the measurements using an automated Parks-Bielschowsky three-step test to identify the weak muscle leading to vertical strabismus. By placing the target shape in an off-center position, the deviation can be measured in different positions of gaze. Referring also to FIG. 4, the combination of these measurements can be output to the secondary display in the form of a Hess chart 70, allowing the examiner to analyze the pattern of strabismus and identify the afflicted neuromuscular pathways. The Hess chart analysis can also be analyzed algorithmically in an automated fashion. In the example of FIG. 4, the Hess chart 70 shows that limited up-and-to-the-right gaze of the right eye is demonstrated due to restriction or weakness of the right inferior oblique muscle (RIO).

Figure 7:
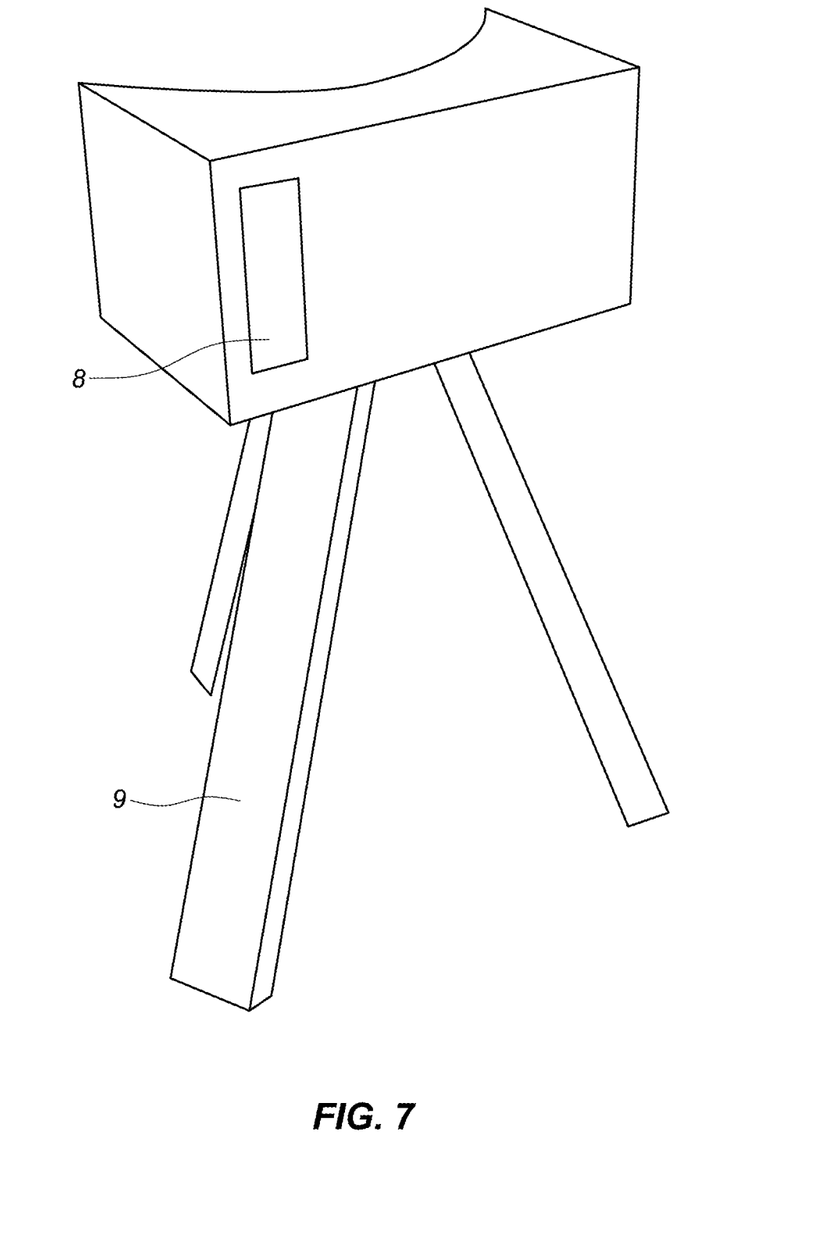
FIG. 7 is a perspective view of another embodiment of a viewer, including a camera associated with the viewer, and a tripod connectable to the viewer.

The extra ocular movements can also be directly examined. Referring also to FIG. 7, in another embodiment, the viewer 20 may be equipped with a camera 8 that can capture the eyes in each of the nine positions of gaze (forward, up, left, down, right, up-and-to-the-right, up-and-to-the-left, down-and-to-the-right, down-and-to-the-left. Each eye is then identified in each image captured by the camera 8 using any of the known computer vision algorithms for this purpose (e.g., neural nets). The corneal limbus can then be identified in the region of interest corresponding using the algorithm described in Pătrăucean V., Gurdjos P., von Gioi R. G. (2012) A Parameterless Line Segment and Elliptical Arc Detector with Enhanced Ellipse Fitting. In: Fitzgibbon A., Lazebnik S., Perona P., Sato Y., Schmid C. (eds) Computer Vision—ECCV 2012. ECCV 2012. Lecture Notes in Computer Science, vol 7573. Springer, Berlin, Heidelberg for ellipse detection, or any other similar computer vision algorithm for the detection ellipse segments. The eccentricity of the ellipse corresponding to the corneal limbus is then used as a quantitative determination of the amount of eye rotation for the implicated eye in a given position of gaze and is output to the examiner, such as in the form of a Hess chart 70 of FIG. 4.

Figure 5:
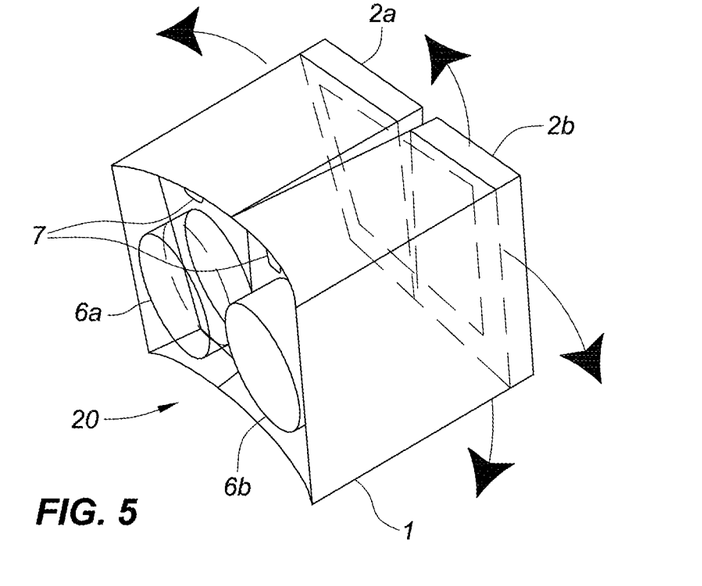
FIG. 5 is a perspective view of another embodiment of a viewer, including two separate displays.

Referring also to FIG. 5, another embodiment of the viewer 20 is shown, in which the screen 2 is split into two screens 2a, 2b, each viewable from a separate ocular 6a, 6b.

The oculars 6a, 6b can swivel relative to each other. The subject swivels the oculars 6a, 6b until the images in the display appear aligned translationally. The horizontal and vertical angles of the oculars 6a, 6b relative to each other are quantified to determine the horizontal and vertical misalignment of the eyes. The physical angle of the two oculars 6a, 6b relative to one another may be determined in any suitable manner, and transmitted to the integrated microprocessor 40. As one example, a standard Cartesian coordinate system is established, where the z axis points forward in the direction of the patient's nose, perpendicular to the frontal plane; the y axis (axial) is up and down (vertical), and the x axis is left and right (horizontal). To determine the angles between the oculars 6a, 6b in the xz and yz planes, two sensors may be used to determine those angles. As one example, those sensors may be potentiometers (not shown) physically coupled to those axes of rotation, so that the angles between the oculars 6a, 6b in the xz and yz planes can be directly measured from the electrical resistance at each of the potentiometers. As in the other embodiments, the images on the displays can be rotated relative to each other to quantify torsional misalignment. Infrared cameras 7 facing the eyes may be used to track the pupil movements, and can provide additional information about ocular misalignment.

FIG. 8 shows yet another variation in which a joystick or other controller 10 is used to provide input to the device by the subject. A PC 11, or other type of remote display, is used to mirror the images seen by the subject and to provide output data to the examiner. The controller and PC may be tethered to the viewer using a wired serial or bus connection 12, or a wireless connection 13 implementing Bluetooth or other wireless communication protocol.

As used in this document, both in the description and in the claims, and as customarily used in the art, the words "substantially," "approximately," and similar terms of approximation are used to account for manufacturing tolerances, manufacturing variations, manufacturing imprecisions, and measurement inaccuracy and imprecision that are inescapable parts of fabricating and operating any mechanism or structure in the physical world.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. The purpose of the Abstract of this document is to enable the U.S. Patent and Trademark Office, as well as readers who are not familiar with patent or legal terms or phraseology, to determine quickly from a cursory inspection the nature and essence of the technical disclosure of the application. The Abstract is not intended to define the invention, nor is it intended to limit to the scope of the invention. Therefore, the invention is not to be restricted or limited except in accordance with the following claims and their legal equivalents.

What is claimed is:

1. A device for measuring and classifying ocular misalignment of a patient's eyes, comprising:
   an enclosure;
   two lenses at the front of said enclosure, one corresponding to each eye of the patient;
   a divider within said enclosure, said divider positioned laterally between said lenses;
   a screen within said enclosure;
   an integrated microprocessor connected to said screen; and
   at least one input control connected to said integrated microprocessor, said at least one input control operable by the patient;
   wherein said integrated microprocessor generates and transmits two images to said screen, each said image corresponding to each said lens; wherein said integrated microprocessor receives input from the patient via said at least one input control to manipulate at least one said image on said screen; and wherein said integrated microprocessor calculates and outputs a quantification of ocular misalignment based on said input.

2. The device of claim 1, further comprising at least one sensor selected from the group consisting of a gyroscope and a gravitometer, said at least one sensor connected to said integrated microprocessor, wherein said integrated microprocessor receives sensor input from said at least one sensor and calculates and outputs a quantification of ocular misalignment based in part on said sensor input.

3. The device of claim 1, further comprising a smartphone, wherein said integrated microprocessor and said screen are part of said smartphone; wherein said enclosure includes a receiver into which said smartphone is placed.

4. The device of claim 1, further comprising a tablet, wherein said integrated microprocessor and said screen are part of said tablet; wherein said enclosure includes a receiver into which said tablet is placed.

5. The device of claim 1, further comprising at least one camera positioned within said enclosure to view the eyes of the patient.

6. The device of claim 1, further comprising a stand connected to said enclosure.

7. The device of claim 1, wherein said at least one input control comprises at least one button located on an outer surface of said enclosure.

8. The device of claim 1, wherein said at least one input control is a joystick.

9. The device of claim 1, further comprising a remote display connected to said integrated microprocessor, wherein said integrated microprocessor outputs said quantification of ocular misalignment to said remote display.

10. The device of claim 1, wherein said lenses are separated from said screen by a distance between substantially 3.5-4.0 cm.

11. A method for measuring and classifying ocular misalignment of a patient by an examiner, comprising:
   providing a viewer, comprising an enclosure, two lenses at the front of said enclosure, one corresponding to each eye of the patient, a divider within said enclosure, said divider positioned laterally between said lenses, and a screen within said enclosure;
   displaying on said screen two different images, one corresponding to each lens, wherein each eye of the patient sees a different image, wherein said displaying is performed independent of control by the examiner;

receiving input from the patient, wherein said input aligns said images based on the patient's perception; and determining the misalignment between the images that remains after said receiving input.

12. The method of claim 11, further comprising:

measuring head tilt of the patient while receiving input from the patient;

wherein said determining utilizes head tilt of the patient.

13. The method of claim 11, wherein said determining said misalignment comprises determining torsional misalignment.

14. The method of claim 11, wherein said determining said misalignment comprises determining horizontal misalignment.

15. The method of claim 11, wherein said determining said misalignment comprises determining vertical misalignment.

16. The method of claim 11, further comprising outputting the results of said determining to the examiner.

17. The method of claim 11, wherein said enclosure includes a slot, and wherein said providing comprises inserting a smartphone into said slot; wherein said screen is part of said smartphone.

18. A device for measuring and classifying ocular misalignment of a patient's eyes, comprising:

two oculars rotatable relative to one another;

two screens, wherein each screen is associated with a separate said ocular;

at least one sensor that determines the rotation of said oculars relative to one another;

an integrated microprocessor connected to each said screen; and wherein said integrated microprocessor generates and transmits two images, one said image transmitted to each said screen; wherein said integrated microprocessor receives input from the patient via said at least one sensor; and wherein said integrated microprocessor calculates and outputs a quantification of ocular misalignment based on said input.

19. The device of claim 18, further comprising at least one input control connected to said integrated microprocessor, said at least one input control operable by the patient.

* * * * *